United States Patent
Block et al.

[11] 3,974,128
[45] Aug. 10, 1976

[54] ESTERS OF MALEIC ANHYDRIDE INTERPOLYMERS

[75] Inventors: Ira Jordan Block; Phillip Edward Sokol, both of Chicago, Ill.

[73] Assignee: The Gillette Company, Boston, Mass.

[22] Filed: Feb. 4, 1974

[21] Appl. No.: 439,263

Related U.S. Application Data

[62] Division of Ser. No. 251,362, May 8, 1972, Pat. No. 3,862,306.

[52] U.S. Cl. ............................... 526/14; 222/192; 424/47; 526/49; 526/271; 526/332
[51] Int. Cl.² .................. C08F 8/14; C08F 222/12
[58] Field of Search ............. 260/78.5 R, 260/78.5 T

[56] References Cited
UNITED STATES PATENTS

| | | | |
|---|---|---|---|
| 3,342,787 | 9/1967 | Muskat | 260/78.5 |
| 3,395,041 | 7/1968 | Hsiung | 132/7 |
| 3,436,378 | 4/1969 | Azorlosa et al. | 260/78.5 |
| 3,625,924 | 12/1971 | Field et al. | 260/78.5 T |
| 3,721,655 | 3/1973 | Schlumbom et al. | 260/78.5 T |

*Primary Examiner*—John Kight, III

[57] ABSTRACT

Water-insoluble alkyl half ester interpolymers and water-insoluble ammonium and amine salts thereof, and hair spray compositions made therefrom; said interpolymers consisting essentially of the structural units:

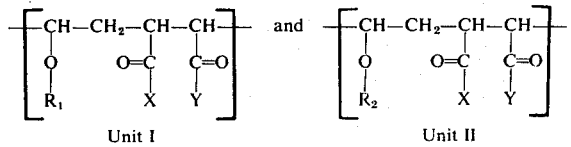

obtained by interpolymerizing maleic anhydride with two different alkyl vinyl ethers, $R_1$—O—CO=$CH_2$ and $R_2$—O—CH=$CH_2$, followed by partial esterification with an alkanol having 1 to 8 carbon atoms.

The esterification can be followed by neutralization of free carboxyl groups with ammonia, a primary, secondary, or tertiary alkylamine, alkanolamine, or alkylalkanolamine of the formula

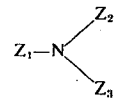

where $Z_1$, $Z_2$, and $Z_3$ are all hydrogen to make up ammonia, where $Z_1$, $Z_2$, and $Z_3$ are individually selected from the group consisting of hydrogen and of alkyl radicals, having 1 to 18 carbon atoms to make up the alkylamine, where $Z_1$, $Z_2$, and $Z_3$ are individually selected from the group consisting of hydrogen and of hydroxyethyl and hydroxypropyl radicals to make up the alkanolamine, or where $Z_1$, $Z_2$, and $Z_3$ are mixtures of alkyl and hydroxyalkyl groups as described to make up the alkylalkanolamine, to give the ammonium or amine salts of the interpolymers.

$R_1$=Alkyl radical, 8 to 18 carbon atoms, $R_2$=Alkyl radical, 1 to 3 carbon atoms; X and Y are individually selected from the group consisting of (1) alkoxy, 1 to 8 carbon atoms, and (2) hydroxy. The ammonium or amine salts of the foregoing compounds (when X or Y represents a hydroxy radical) are salts of ammonia or of those amines described above.

10 Claims, No Drawings

ESTERS OF MALEIC ANHYDRIDE INTERPOLYMERS

This is a division of application Ser. No. 251,362, filed May 8, 1972, now U.S. Pat. No. 3,862,306.

This invention relates to novel water-insoluble film-forming derivatives of maleic anhydride interpolymers and to novel hair-setting compositions incorporating these derivatives of interpolymers.

In the art of imparting a temporary set to a configuration of the hair to obtain a particular hair style by means of hair-setting compositions or hair sprays, the desired effect is to have sufficient set-holding of the hair to withstand even adverse weather conditions such as brisk wind or high humidity without making the hair excessively stiff, tacky, or difficult to comb or without leaving flakes in the hair. Present hair sprays afford some set holding properties without accentuating these undesired characteristics, but they do not approach effective set-holding under adverse weather conditions without imparting either excessive stiffness, tack, or otherwise aggravating the aforementioned unwanted properties.

One object of the present invention is to provide new compositions of matter.

A further object is to provide a hair-setting composition which displays remarkably improved set-holding characteristics and which maintains the coiffure in the desired configuration even under adverse conditions such as high temperature and high humidity.

A further object is to provide a hair-setting composition which maintains the coiffure in the desired configuration without leaving the hair excessively stiff and inflexible.

Another object is to provide a hair-setting composition which retains a dry non-tacky surface even when exposed to conditions of high humidity.

Still another object is to provide a hair-setting composition which makes it possible to comb the hair without difficulty.

A further object is to provide a hair-setting composition which is capable of being homogeneously blended with gaseous or liquefied gas pressure propellants, particularly halogenated hydrocarbon propellants, in order to be dispensed from a pressure container in the form of an aerosol.

Other and further objects will be apparent from the description which follows.

The resins of this invention are certain water-insoluble film-forming modified interpolymers of maleic anhydride and two different alkyl vinyl ethers. More specifically, they are water-insoluble lower alkyl half esters of maleic anhydride interpolymer compounds and water-insoluble ammonium and amine salts thereof which are comprised of repeating groups of the formula

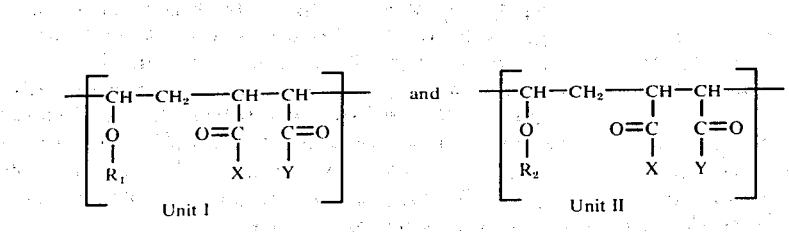

wherein $R_1$ represents an alkyl radical containing 8 to 18 carbon atoms, $R_2$ is an alkyl radical having from one to three carbon atoms, and X and Y are each individually selected from the group consisting of (1) an alkoxy radical containing 1 to 8 carbon atoms and of (2) the hydroxy radical. The ammonium and amine salts of the foregoing compounds (when X or Y represents a hydroxy radical) are salts of ammonia, a primary, secondary or tertiary alkylamine, alkanolamine, or alkylalkanolamine of the formula

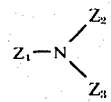

where $Z_1$, $Z_2$, and $Z_3$ are all hydrogen to make up ammonia, where $Z_1$, $Z_2$, and $Z_3$ are individually selected from the group consisting of hydrogen and of alkyl radicals, having 1 to 18 carbon atoms to make up the alkylamine, where $Z_1$, $Z_2$, and $Z_3$ are individually selected from the group consisting of hydrogen and of hydroxyethyl and hydroxypropyl radicals to make up the alkanolamine, or where $Z_1$, $Z_2$, and $Z_3$ are mixtures of alkyl and hydroxyalkyl groups as described to make up the alkylalkanolamine. The proportion of alkoxy groups in the total number of groups X and Y is from about 40 percent to about 60 percent; there being from about 0.01 to about 43 mole percent of Unit I and from about 57 to about 99.99 mole percent of Unit II in the interpolymer.

Examples of the alkyl radical $R_1$ are n-octyl, dodecyl, hendecyl, tridecyl, tetradecyl, hexadecyl, and stearyl. The members of the alkyl radical $R_2$ group are methyl, ethyl, n-propyl, and isopropyl. Examples of the alkoxy radicals comprising one of the groups from which X or Y is selected are methoxy, ethoxy, isopropoxy, n-pentoxy, hexoxy, and heptoxy.

The molecular weight of the instant anhydride interpolymers of this invention may be conveniently defined by their viscosity as an alcohol solution of the alkyl half ester which can be measured using the Brookfied Viscometer. The interpolymers of this invention exhibit a Brookfield viscosity from about 100 cps. to about 4000 cps. at 25°C and at 30% concentration in ethanol using a No. 2 spindle with a 250 cc. beaker, the percentage being based on the weight of the total solution; those polymers giving a Brookfield viscosity from about 200 cps. to about 3000 cps. under the same conditions are preferred.

These novel water-insoluble derivatives of interpolymers can be prepared by conventional known methods by interpolymerizing maleic anhydride and a mixture of alkyl vinyl ethers using approximately 1 mole of maleic anhydride per mole of alkyl vinyl ether mixture. One class of alkyl vinyl ether may be represented by the structural formula

wherein $R_1$ represents an alkyl radical containing 8 to 18 carbon atoms, preferably a substantially linear (long chain) moiety. The other class of alkyl vinyl ether may be represented by the structural formula $$R_2-O-CH=CH_2$$

wherein $R_2$ represents an alkyl radical containing 1 to 3 carbon atoms. The ratio of the $R_1-O-CH=CH_2$ alkyl vinyl ether to the $R_2-O-CH=CH_2$ alkyl vinyl ether comprising the total amount of such vinyl ether mixtures should be within the ranges mentioned above, i.e., from about 0.01 to about 43 mole percent of the $R_1-O-CH=CH_2$ alkyl vinyl ether and from about 57 to about 99.99 mole percent of the $R_2-O-CH=CH_2$ alkyl vinyl ether. This ratio can also be defined in terms of the relative weights of the two ethers in which case the ranges would be from about 2 to about 75 weight percent of the $R_1-O-CH=CH_2$ ether and from about 25 to about 98 weight percent of the $R_2-O-CH=CH_2$ ether, based on the total weight of the vinyl ether mixture.

The polymerization is carried out by adding a catalytic amount of an organic free-radical-generating initiator to a mixture of the three monomers in a diluent. The mixture is heated thoroughly so that the polymerization reaction takes place to produce the anhydride interpolymer containing repeating units of the formula

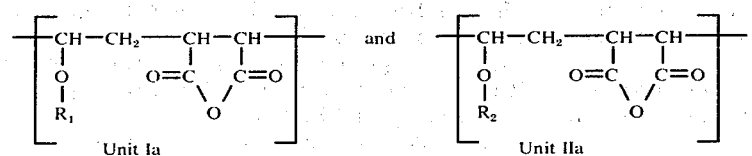

wherein $R_1$ and $R_2$ are as above defined. When gas chromatographic analysis indicates no detectable residual monomer, the polymer is postcooked and isolated from the diluent by any suitable means such as distillation.

The diluent selected can include benzene, xylene, toluene, acetone, methyl ethyl ketone, and the like. If desired, the reaction can also be conducted in an inert atmosphere such as nitrogen, argon and the like.

Suitable organic initiators include, for example, benzoyl peroxide, lauroyl peroxide, caprylyl peroxide, acetyl peroxide, acetyl benzoyl peroxide, di-tert-butyl peroxide, dimethyl azobisisobutyrate, azobisisobutyronitrile, and the like. Radiation polymerization is also suitably conducted using initiators such as high energy radiation sources, for example, X-rays, gamma rays, ultraviolet light, neutrons, and the like.

The polymerization can be performed at a temperature within the range of about 0° to about 150°C, preferably in the range from about 45°C to about 100°C, particularly about 80°C.

Conversion of this anhydride interpolymer containing repeating units of the formula of Units Ia and IIa to the water-insoluble film-forming half esters of this invention, Units I and II, is accomplished by reacting the interpolymers with an alkanol containing from 1 to 8 carbon atoms such as ethanol, isopropanol, n-butanol, pentanol, hexanol, or heptanol. Each anhydride group, upon reacting, forms (1) a carboxylic ester group and, simultaneously, (2) a carboxylic acid group. The carboxylic acid groups so formed can themselves be reacted to form additional ester groups. Consequently, the modified interpolymer can be defined as one in which from 40% to 60%, preferably about 50%, of the total carboxyl groups (the total which could be formed by hydrolysis of all the anhydride groups) present in the interpolymer are reacted to form esters, the remaining carboxyl groups existing as free carboxyl groups.

The esterification of the interpolymers is a substantially spontaneous reaction where the half ester is desired. The reaction with the alkanol is best carried out by heating the mixture at reflux temperature. To be certain that 50% of the total carboxyl groups (the total which could be formed by hydrolysis of all the anhydride groups) are esterified, the mixture may be heated up to 25 to 50 hours at reflux temperature. Alternatively, infrared spectroscopy can be used to determine the absence of anhydride units indicating total conversion to carboxyl and carboxylic ester groups.

The esterification process can be started simultaneously with the removal of the diluent as for example by azeotropic distillation of the benzene diluent with ethanol. Continued refluxing in ethanol under the aforesaid conditions will give complete half ethyl ester formation. The half ester is soluble in the alkanol used in the esterification. The alkanol solution is then concentrated to a convenient form, about 30 to 45 weight percent solids based on the total weight of the solution.

Additionally the free carboxyl groups can undergo neutralization in order to produce the water-insoluble ammonium or amine salts of this invention. This neutralization can be carried out at room temperature by adding to the partial alkyl esters ammonia, a primary, secondary, or tertiary alkylamine, alkanolamine, or alkylalkanolamine of the formula

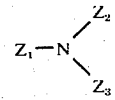

where $Z_1$, $Z_2$, and $Z_3$ are all hydrogen to make up ammonia where $Z_1$, $Z_2$, and $Z_3$ are individually selected from the group consisting of hydrogen and of alkyl radicals, having 1 to 18 carbon atoms to make up the alkylamine, where $Z_1$, $Z_2$, and $Z_3$ are individually selected from the group consisting of hydrogen and of hydroxyethyl and hydroxypropyl radicals to make up the alkanolamine, or where $Z_1$, $Z_2$, and $Z_3$ are mixtures of alkyl and hydroxyalkyl groups as described to make up the alkylalkanolamine, to give the ammonium or amine salts of the interpolymers.

Where an alkylamine is utilized, suitable amines include primary alkylamines having 1 to 18 carbon atoms such as ethylamine, n-propylamine, n-butylamine, n- heptylamine, n-decylamine, laurylamine, or stearylamine; secondary alkylamines consisting of alkyl branches having from 1 to 18 carbon atoms each such as dimethylamine, diisopropylamine, ethylisopropylamine, methyl-n-hexylamine, laurylmethylamine, or dioctylamine; and tertiary alkylamines consisting of alkyl branches having from 1 to 18 carbon atoms each such as triethylamine, triisopropylamine, tri-n-butylamine, lauryldimethylamine, stearyldimethylamine, or trioctylamine. Stearyldimethylamine is preferred.

Where an alkanolamine is utilized, suitable alkanolamines include mono-, di-, and tri-ethanolamine and isopropanolamine. Triethanolamine is the preferred reagent.

Where an alkylalkanolamine is utilized, suitable alkylalkanolamines include bis-hydroxyethylstearylamine, bis-hydroxypropyllaurylamine, hydroxyethyldibutylamine, or hydroxypropyldioctylamine.

Of the remaining carboxyl groups which exist as free carboxyl groups, from about 5 to 50% can be neutralized to form the ammonium, alkylamine, alkanolamine, or alkylalkanolamine salts. Preferably from about 10 to 20% can be neutralized.

The hair-setting compositions of this invention comprise the half ester interpolymers and the ammonium and amine salts thereof described above dissolved in an anhydrous alkanol containing from 1 to 8 carbon atoms such as ethanol, n-propanol, isopropanol, the butanols, pentanol, and hexanol. The solution should contain from about 0.05 percent to 20 percent, preferably from 0.5 percent to 10 percent, by weight of the total solution, of the interpolymer.

While this solution of the film-forming material in the alkanol may be applied to the hair by an atomizer or in any other suitable fashion, it has been found most convenient to employ a gaseous or volatile liquid propellant and to package the mixture of propellant with the alcoholic solution in a pressure package having a valve-controlled outlet. Any of the usual propellants may be employed, such as propane, isobutane, or, preferably, the saturated halogenated aliphatic hydrocarbons known by the trade name "Freon" and which include, for example, 1,1-difluoroethane; 1,2-dichloro-1,1,2,2-tetrafluoroethane; trichlorotrifluoroethane; dichlorodifluoromethane; monochlorodifluoromethane; monofluorotrichloromethane; 1-monochloro-1,1-difluoroethane; or mixtures thereof. With the propellant included, the half ester and ammonium and amine salt interpolymers constitute from about 0.5 to about 10 percent by weight of the total composition; preferably from about 0.5 to about 4 percent. Similarly, the alkanol solvent constitutes from about 35 to about 64.5 percent by weight of the total composition; preferably from about 45 to 54.5 percent. The liquefied gas propellant constitutes from about 35 to 64.5 percent by weight of the total composition; preferably from about 45 to about 54.5 percent.

Optionally, the composition can include conventional additives known in the hair spray art such as a plasticizer, perfume, and a conditioning agent. Optional plasticizers may include such compounds as isostearyl alcohol, diisopropyl adipate, dibutyl phthalate, and isopropyl stearate. The amount of plasticizer can vary from about 0.05 to about 20 percent by weight of the interpolymer; preferably about 1 to 20 percent. Preferably, based on the weight of the total composition, the plasticizer should range from about 0.05 to about 3 percent.

Minor amounts of other conventional additives such as lanolin to restore the natural condition of the hair, liquid dimethyl polysiloxane for ease in combing (from 1 to 20 percent by weight of the polymer), and an alcohol soluble perfume for aesthetic appeal (from 0.1 to about 1 percent by weight of the total composition) may also be included.

The following specific examples are intended to illustrate more clearly the nature of the present invention without acting as a limitation upon its scope.

EXAMPLE 1

An interpolymer containing equimolar amounts of maleic anhydride and of a mixture of stearyl vinyl ether and ethyl vinyl ether in which 5 percent by weight of the ether mixture was stearyl vinyl ether and 95 percent was ethyl vinyl ether was prepared as follows: A mixture of 262 parts by weight of maleic anhydride, 10 parts by weight of stearyl vinyl ether, and 190 parts by weight of ethyl vinyl ether was prepared to which was added lauroyl peroxide in an amount totaling 0.5 percent by weight of the mixture. The monomer mixture containing the initiator was added to 2300 parts of refluxing benzene over a one-half hour period. Refluxing was continued an additional 1–2 hours. The benzene was then removed, first by distillation and then finally by azeotroping it with ethanol during which a portion of the interpolymer (in anhydride form) was converted to the half ethyl ester. Continued refluxing in ethanol resulted in complete half ester formation. Finally, the ethanol solution was concentrated to about 30 to 40 percent polymer solids by weight of total solution.

The solution was then diluted with additional ethanol to form a mixture of about 2 parts by weight of the interpolymer to 47.3 parts by weight of ethanol. To this mixture there was added 0.3 parts by weight of isopropyl stearate, 0.3 parts by weight of stearyldimethylamine, and 0.1 parts by weight of perfume. This solution was then charged into a pressure container along with 32 parts by weight of Freon 11 and 18 parts by weight of Freon 12, the Freon propellants being maintained in liquefied form within the pressure container (pressure about 36–40 p.s.i.g.).

When sprayed on a hair tress held in a desired configuration and allowed to dry, the composition was found to provide good set-holding characteristics even under conditions of high humidity while at the same time leaving the hair neither excessively stiff, tacky, nor powdery.

EXAMPLE 2

A half ethyl ester interpolymer containing equimolar amounts of maleic anhydride and a vinyl ether mixture of 25 percent by weight of stearyl vinyl ether and 75 percent by weight of ethyl vinyl ether was prepared according to the procedures described in Example 1.

The interpolymer was then dissolved in ethanol to the same concentration as in Example 1, and the same additives in the same weight proportions were added as in Example 1 with the exception that 0.3 parts by weight of isostearyl alcohol were used in place of isopropyl stearate. The solution was then charged into a pressure container along with volatile propellants as described in Example 1 above. When sprayed on a hair tress, it was found to have substantially the same set-holding characteristics as the composition of Example 1 and likewise without imparting excessive stiffness, tackiness, or flakiness to the hair.

EXAMPLE 3

A half ethyl ester interpolymer containing equimolar amounts of maleic anhydride and a vinyl ether mixture of 75 percent by weight of stearyl vinyl ether and 25 percent by weight of ethyl vinyl ether was prepared according to the procedures described in Example 1.

The interpolymer was then further diluted in ethanol, and a hair spray composition was prepared using the same weight proportions of polymer, ethanol, and the same conventional additives as in Example 1 with the exception that 0.45 parts by weight of diisopropyl adipate were used instead of the isopropyl stearate. The solution was charged into a pressure container along with volatile propellants as described in Example 1 above. When sprayed on a hair tress, it was found to have substantially the same set-holding characteristics and other aforementioned desirable characteristics as the composition of Example 1.

EXAMPLE 4

In the same manner as outlined in Example 1, an ethyl half ester interpolymer was prepared containing equimolar amounts of maleic anhydride and a vinyl ether mixture of 25 percent by weight of cetyl vinyl ether and 75 percent by weight of ethyl vinyl ether. The reaction solution was then formulated into a hair spray in the same manner as in Example 1. Similar desirable set-holding characteristics were found upon use.

EXAMPLE 5

In the same manner as outlined in Example 1, an ethyl half ester interpolymer was prepared containing equimolar amounts of maleic anhydride and a vinyl ether mixture of 25 percent by weight of decyl vinyl ether and 75 percent by weight of ethyl vinyl ether. The reaction solution was then formulated into a hair spray in the same manner as in Example 1. Similar desirable set-holding characteristics were found upon use.

Similar results as regards set-holding were obtained using solutions prepared as described above, containing the water-insoluble ethyl half esters of interpolymers composed of equimolar amounts of maleic anhydride and the following vinyl ether mixtures:

1. 25 percent by weight of isooctyl vinyl ether and 75 percent by weight of ethyl vinyl ether.
2. 25 percent by weight of stearyl vinyl ether and 75 percent by weight of methyl vinyl ether.
3. 25 percent by weight of lauryl vinyl ether and 75 percent by weight of ethyl vinyl ether.
4. 25 percent by weight of stearyl vinyl ether and 75 percent by weight of n-propyl vinyl ether.

The percentage of each ether is based on the total weight of the mixture of the two alkyl vinyl ethers used in each case.

The set-holding properties of the hair-setting compositions of the present invention were tested by the following procedure:

Moderately wet 5 inch tresses of straight hair are wrapped around a ¾ inch diameter curler and secured with a large bobbi pin. Tresses are dried at room temperature or in a 45°C. oven if speed is desired. The hair fibers are secured with a small bobbi pin at the backside of the curl, while the original large bobbi pin is removed and the curler is carefully slid out of the curl. Each tress is sprayed two seconds from approximately 8 inches with the particular hair-set composition to be tested. Usually samples are done in duplicate or triplicate. After the samples have air dried for one-half hour, the bobbi pin is carefully removed and the samples are placed on a suspension rod. The initial curl fall is recorded in centimeters — measuring from the bottom edge of the tress card to the bottom edge of the curl. Then the samples are placed in an 85 percent relative humidity chamber or if desired in the 65 percent relative humidity room. The samples are removed for recording data after 2 hours, 4 hours, and overnight exposure. The relative curl fall may be easily calculated if the control spray is given a value of 1.0.

Upon testing as described above all of the compositions of the present invention exhibited substantially the same set-holding capability together with desirable softness of the treated hair. There was no evidence of flaking or powdering in the case of the compositions of the present invention and little or no tendency to exhibit any tackiness upon exposure to conditions of high relative humidity.

What is claimed is:

1. A water-insoluble interpolymer consisting essentially of the structural units:

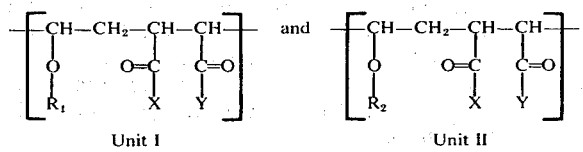

wherein $R_1$ represents an alkyl radical having from 8 to 18 atoms; wherein $R_2$ represents an alkyl radical having from 1 to 3 carbon atoms; and wherein X and Y each independently represent a radical selected from the group consisting of (1) an alkoxy radical having from 1 to 8 carbon atoms and (2) the hydroxy radical; the proportion of alkoxy radicals in the total number of X and Y radicals being from about 40 percent to about 60 percent; there being from about 0.01 to about 43 mole percent of Unit I and from about 57 to about 99.99 mole percent of Unit II in the interpolymer, based on the total number of moles of structural Units I and II in the interpolymer; the Brookfield viscosity of said interpolymer being from about 100 cps. to about 4,000 cps. at 25°C. and at 30% concentration in ethanol using a No. 2 spindle with a 250 cc. beaker, the percentage being based on the weight of the total solution.

2. A water-insoluble interpolymer, according to claim 1, wherein the free carboxyl groups of said interpolymer have been neutralized by ammonia, a primary, secondary, or tertiary alkylamine, alkanolamine, or alkylalkanolamine of the formula

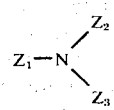

where $Z_1$, $Z_2$, and $Z_3$ are all hydrogen to make up ammonia, where $Z_1$, $Z_2$, and $Z_3$ are individually selected from the group consisting of hydrogen and of alkyl radicals having 1 to 18 carbon atoms to make up the alkylamine, where $Z_1$, $Z_2$, and $Z_3$ are individually selected from the group consisting of hydrogen and of hydroxyethyl and hydroxypropyl radicals to make up the alkanolamine, or where $Z_1$, $Z_2$, and $Z_3$ are mixtures of alkyl and hydroxyalkyl groups as described to make up the alkylalkanolamine, to give the ammonium or amine salts of said interpolymer.

3. A water-insoluble interpolymer, according to claim 2, wherein from about 5 to about 50 percent of the free carboxyl groups of said interpolymer have been neutralized to form the ammonium, alkylamine, alkanolamine, or alkylalkanolamine salts.

4. A water-insoluble interpolymer, according to claim 1, wherein the Brookfield viscosity is from about 200 cps. to about 3000 cps. at 25°C and at 30 percent concentration in ethanol using a No. 2 spindle with a 250 cc. beaker, the percentage being based on the weight of the total solution.

5. A water-insoluble interpolymer, according to claim 1, wherein $R_1$ is a stearyl radical and wherein $R_2$ is an ethyl radical.

6. A water-insoluble interpolymer, according to claim 5, wherein the free carboxyl groups have been neutralized according to claim 3 to give the ammonium or amine salts of said interpolymer.

7. A water-insoluble interpolymer, according to claim 6, wherein X and Y each independently represent a radical selected from the group consisting of (1) an ethoxy radical and (2) an hydroxy radical; the proportion of ethoxy radicals in the total number of X and Y radicals being from about 40 percent to about 60 percent.

8. A water-insoluble interpolymer, according to claim 7, wherein the free carboxyl groups have been neutralized according to claim 3 to give the ammonium or amine salts of said interpolymer.

9. A water-insoluble interpolymer, according to claim 1, wherein $R_1$ is a stearyl radical and wherein $R_2$ is a methyl radical.

10. A water-insoluble interpolymer, according to claim 9, wherein the free carboxyl groups have been neutralized according to claim 3 to give the ammonium or amine salts of said interpolymer.

\* \* \* \* \*

UNITED STATES PATENT AND TRADEMARK OFFICE
CERTIFICATE OF CORRECTION

PATENT NO. : 3,974,128
DATED : August 10, 1976
INVENTOR(S) : Ira Jordan Block et al.

It is certified that error appears in the above-identified patent and that said Letters Patent are hereby corrected as shown below:

Column 1, line 43, "homogeneously" is misspelled;

Column 8, line 36, after "18", insert --carbon--.

Signed and Sealed this

Twenty-third Day of November 1976

[SEAL]

*Attest:*

RUTH C. MASON
*Attesting Officer*

C. MARSHALL DANN
*Commissioner of Patents and Trademarks*